United States Patent [19]
Lu

[11] Patent Number: 5,431,632
[45] Date of Patent: Jul. 11, 1995

[54] SAFETY SYRINGE FOR INTRAVENOUS INJECTION WITH EXTERNALLY CONNECTABLE AND INTERNALLY RETRACTABLE SELF-BIASED NEEDLE

[76] Inventor: Wen-Chin Lu, P.O. Box 10160, Taipei, Taiwan

[21] Appl. No.: 334,159

[22] Filed: Nov. 4, 1994

[51] Int. Cl.$^6$ .............................................. A61M 5/00
[52] U.S. Cl. ..................................... 604/110; 604/195
[58] Field of Search ............... 604/110, 195, 192, 198, 604/187, 263

[56] References Cited

U.S. PATENT DOCUMENTS

| | | | |
|---|---|---|---|
| 4,804,370 | 2/1989 | Haber et al. | 604/110 |
| 5,104,378 | 4/1992 | Haber et al. | 604/110 |
| 5,242,402 | 9/1993 | Chen | 604/110 |
| 5,328,475 | 7/1994 | Chen | 604/110 |

Primary Examiner—John D. Yasko

[57] ABSTRACT

A safety syringe for intravenous injection, includes: a hollow needle assembly having a hollow needle portion detachably coupled to a shank portion embedded in a sleeve portion eccentrically formed on a syringe and having a needle head portion formed on a rear portion of the shank portion, and a plunger straightly slidably held in the syringe without being rotatable and having a biasing socket eccentrically recessed in the plunger for engaging the needle head portion of the needle assembly for a coupling of the needle assembly with the plunger for a retraction together into the syringe for obliquely biasing the needle portion for preventing re-protrusion of the needle outwardly, thereby allowing a variety of needles of different sizes to be replaceably mounted on the shank portion outside the syringe for a convenient mounting of the needle on the syringe.

2 Claims, 6 Drawing Sheets

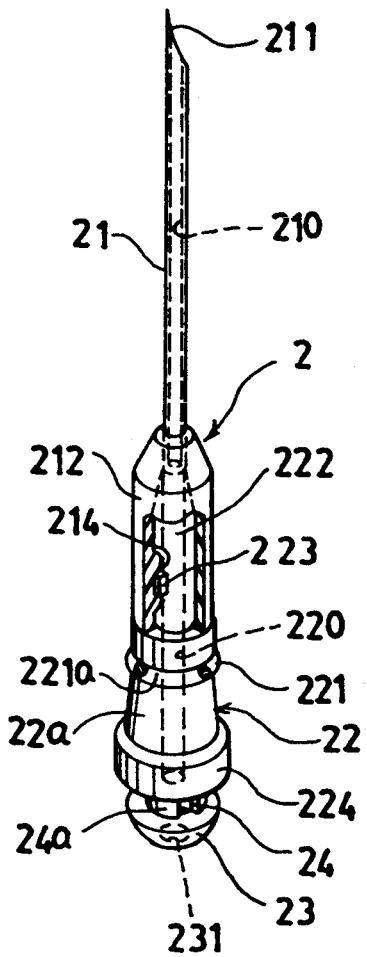
F I G. 5
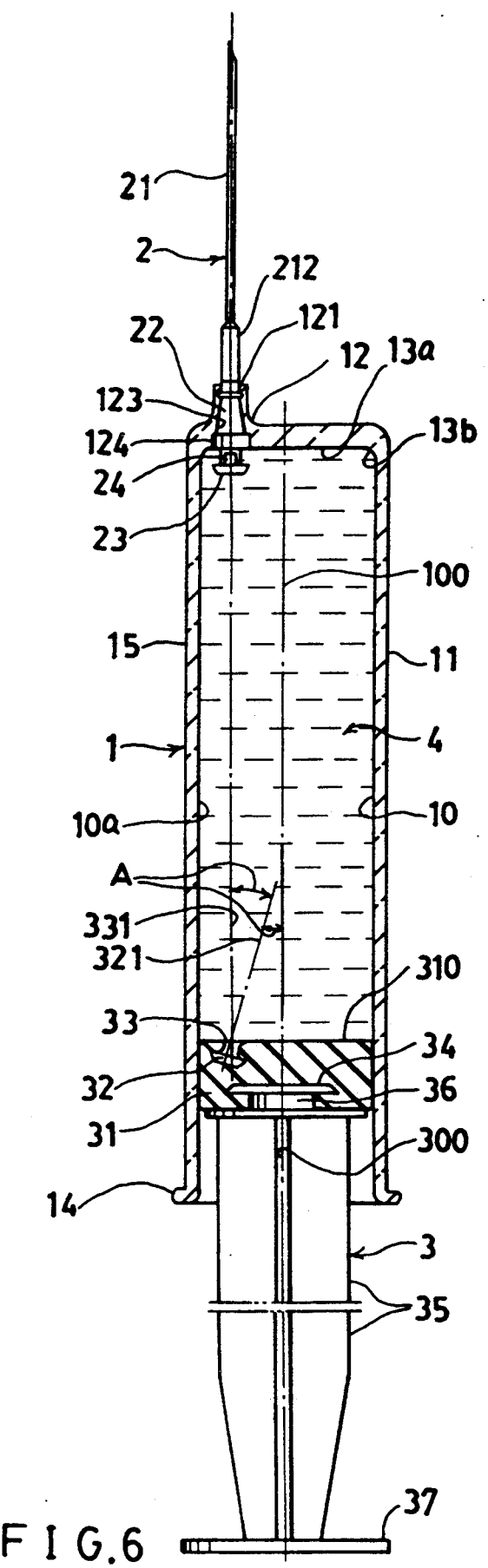
F I G. 6

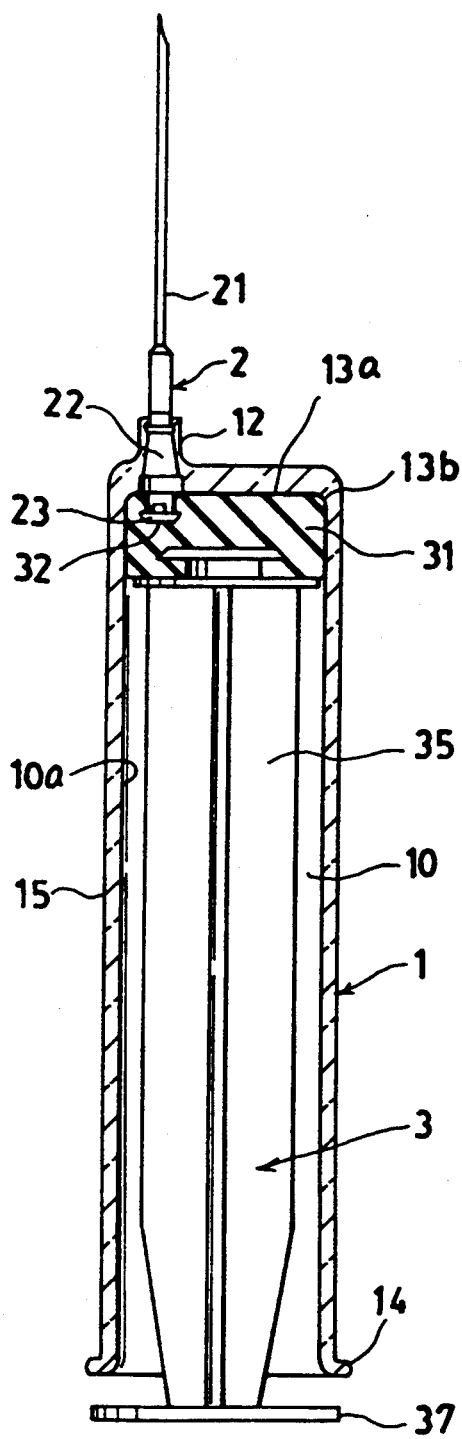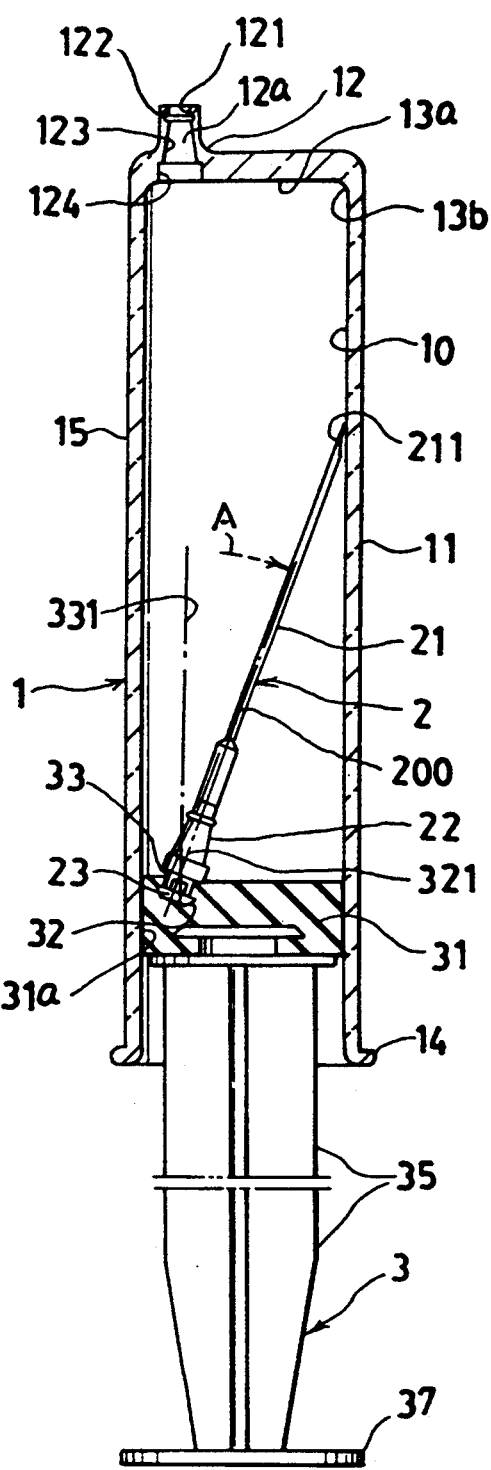
F I G. 7
F I G. 8

SAFETY SYRINGE FOR INTRAVENOUS INJECTION WITH EXTERNALLY CONNECTABLE AND INTERNALLY RETRACTABLE SELF-BIASED NEEDLE

BACKGROUND OF THE INVENTION

U.S. Pat. No. 5,242,402 to Long-Hsiung Chen disclosed a safety syringe for intravenous injection including: an annular groove annularly recessed in a front surface of a plunger slidably held in the syringe to be engageable with a needle head portion formed on a rear portion of a hollow needle eccentrically mounted in a front portion of the syringe, with the annular groove having a longitudinal section formed as a biasing socket engageable with the needle head portion for biasing the needle obliquely within the syringe when retracting the plunger and the needle into the syringe, thereby preventing an outward protruding of the retracted needle for safety and hygienic purpose.

However, such a conventional safety syringe may have the following drawbacks:

1. When engaging the needle head portion 23 of the needle device 2 with the biasing socket of annular groove 32 of the plunger 31 for retracting a used needle into the syringe, the needle head portion 23 may still be released from the annular groove 32 to be accidentally protruded outwardly through the tunnel 130 since the groove 32 is concentrically recessed in the plunger 31, not a single round socket for tightly engaging the needle head portion 23.

2. After retracting the needle in the syringe cylinder, the plunger may still be rotated or twisted to re-protrude the retracted needle outwardly to cause dangerous pricking since the plunger 31 can be free rotational about the syringe axis 100 within the syringe means 1.

3. In order to repel the liquid medicine filled in the annular groove 32, the extension 15 must be provided on a rear surface of the front plug 13 for engaging the groove 32. If the extension 15 is engaged with the groove 32 too tightly, the plug 13 as coupled with the plunger 31 straightly holding the needle 2 will be together retracted inwardly into the cylinder 11, without biasing the needle obliquely.

4. The needle 2 should be inserted through the plug in the syringe cylinder to be mounted on the syringe to cause inconvenience. Also, it can not be replaced with needles of different sizes from outside the syringe.

The present inventor has found the drawbacks of the conventional safety syringe and invented the present safety syringe with externally connectable needle.

SUMMARY OF THE INVENTION

The object of the present invention is to provide a safety syringe for intravenous injection including: a hollow needle assembly having a hollow needle portion detachably coupled to a shank portion embedded in a sleeve portion eccentrically formed on a syringe and having a needle head portion on a rear portion of the shank portion, and a plunger having a cross section of secant circular shape to be straightly slidably held in the syringe having a hollow bore portion also made as a secant circular cross section slidably engageable with the secant plunger and having a biasing socket recessed in the plunger for engaging the needle head portion of the needle assembly for ensuring a straight and sharp coupling of the needle assembly with the plunger for retraction into the syringe for obliquely biasing the needle portion for preventing a re-protrusion of the needle outwardly, whereby a variety of needles of different sizes can be replaceably mounted on the shank portion outside the syringe for a convenient mounting of the needle on the syringe.

BRIEF DESCRIPTION OF THE DRAWINGS

FIG. 5 is a perspective view of the hollow needle assembly.

FIG. 6 is a sectional drawing showing a practical application of the present invention for injection.

FIG. 7 is a sectional drawing of the present invention showing a finished condition after the injection.

FIG. 8 is an illustration showing a self-biased needle when retracted in the syringe cylinder in accordance with the present invention.

DETAILED DESCRIPTION

Figure 1:
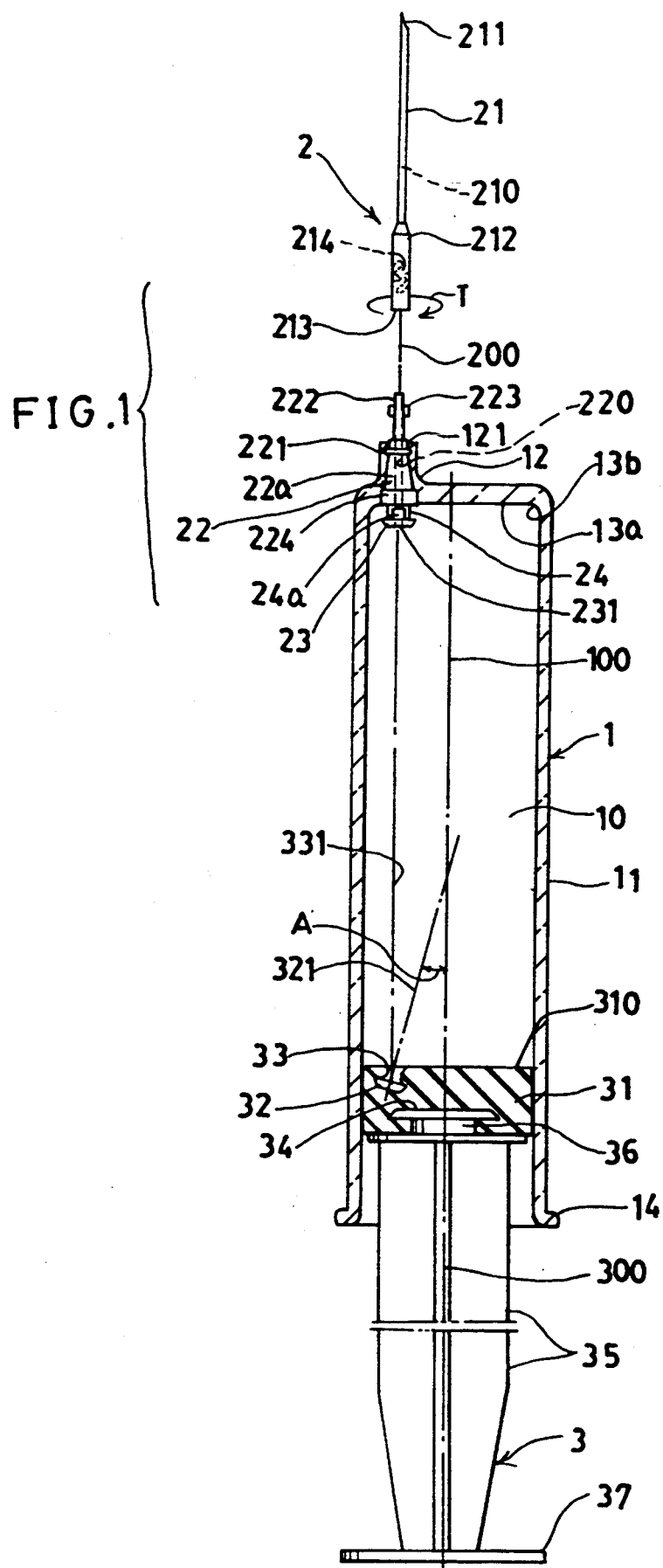
FIG. 1 is a sectional drawing showing all parts in construction of the present invention.
Figure 2:
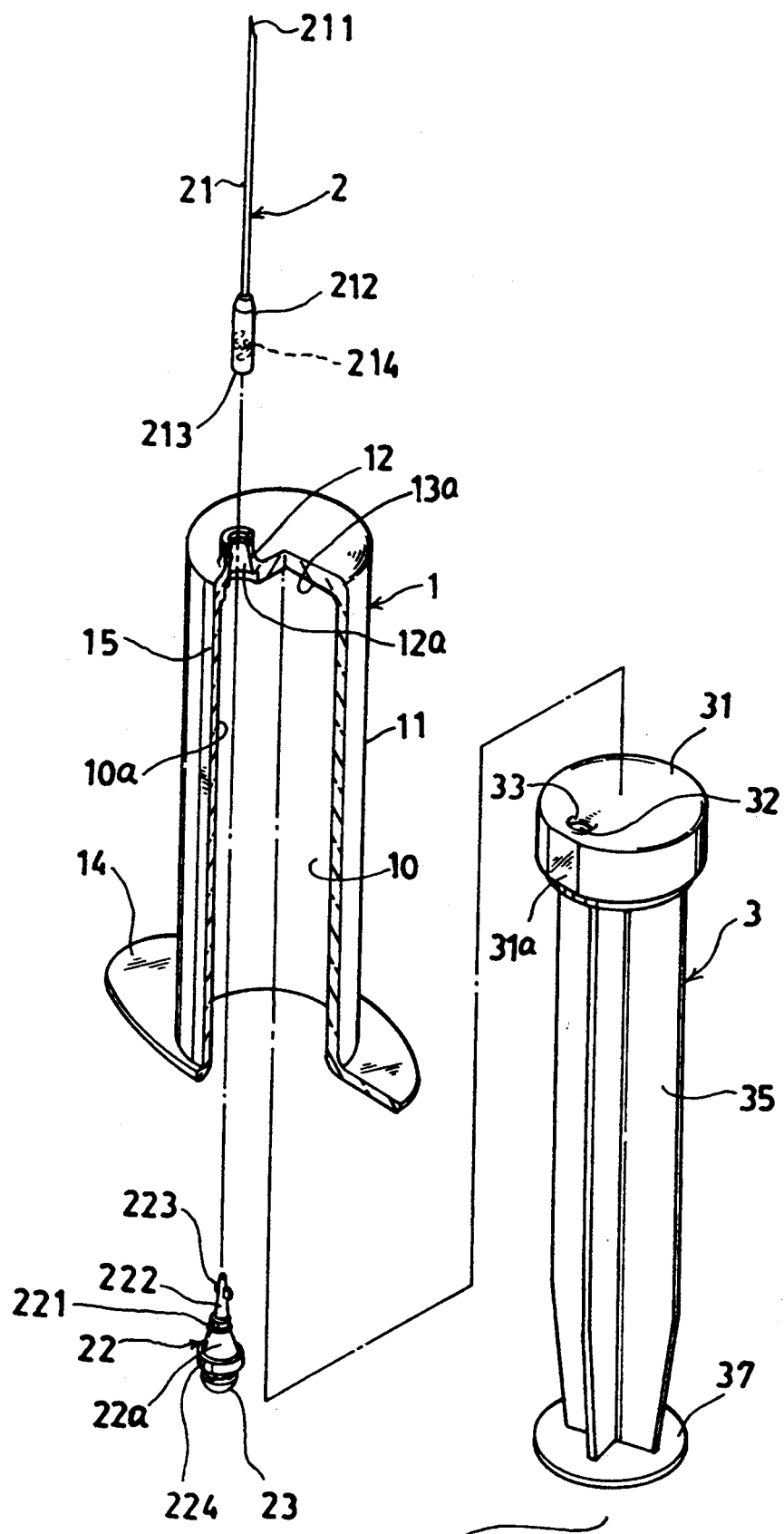
FIG. 2 is an exploded view of the present invention.
Figure 3:
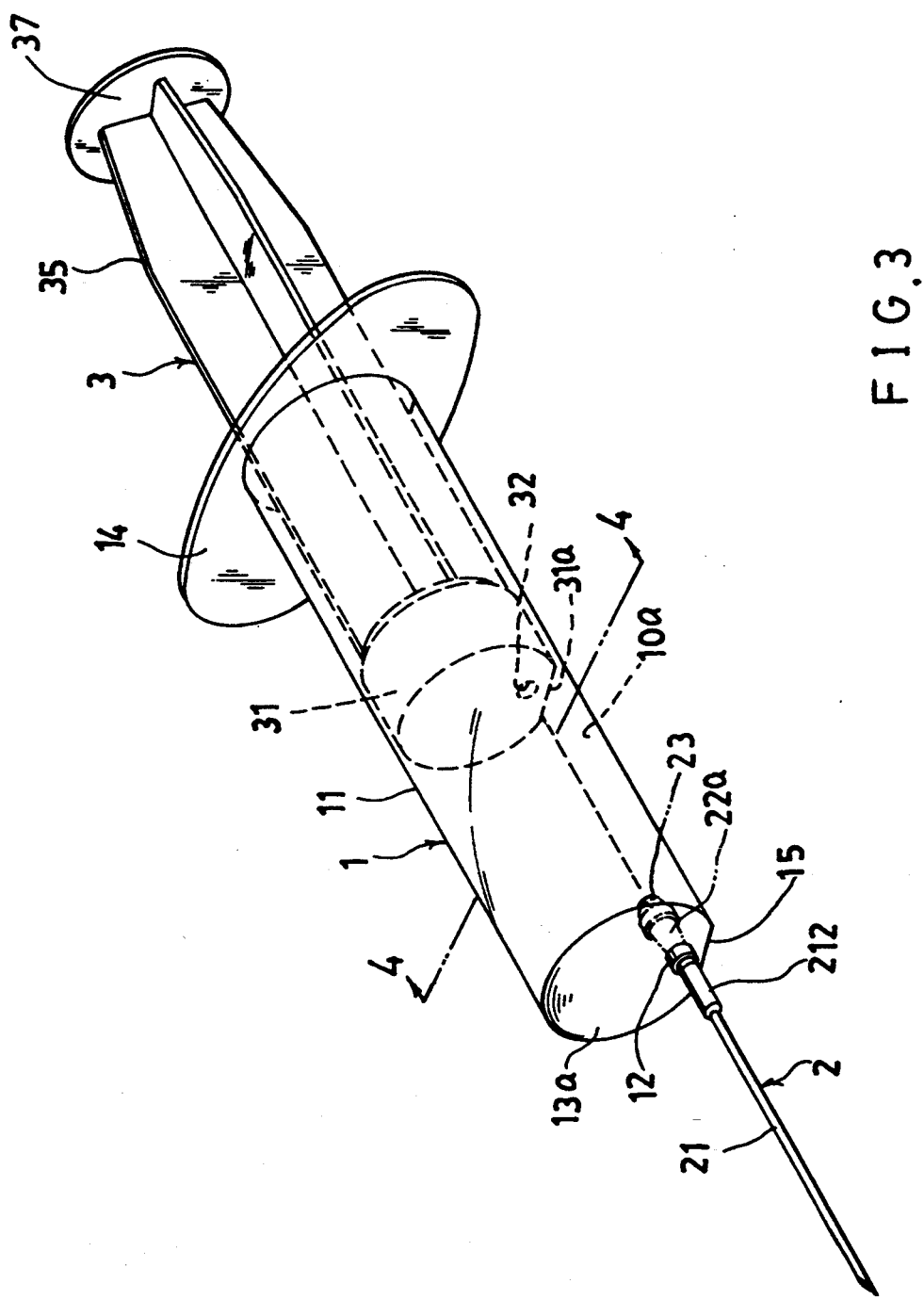
FIG. 3 is a perspective view of the present invention when assembled.

As shown in FIGS. 1-9, the present invention comprises: a syringe means 1, a hollow needle assembly 2 eccentrically mounted on the syringe means 1, and a plunger means 3 straightly slidably held in the syringe means 1.

The syringe means 1 includes: a syringe cylinder 11 having a hollow bore portion 10 formed in the syringe cylinder 11 for filling liquid medicine 4 therein and a syringe axis 100 longitudinally defined in a central portion of the syringe cylinder 11, a sleeve portion 12 eccentrically formed in a front portion of the cylinder 11 contracted and tapered forwardly from a shoulder portion 13a formed in a front portion of the cylinder 11 between the cylinder 11 and the sleeve portion 12, and a syringe handle 14 formed on a rear end portion of the cylinder 11. The cylinder 11 has a flat portion 15 having a cross section of secant circular shape and longitudinally formed on an outside bottom portion of the cylinder 11. The bore 10 is also formed with a flat bore portion 10a inside the cylinder 11.

The sleeve portion 12 includes: a sheath opening 121 formed in a front end portion of the sleeve portion 12, a ring groove 122 annularly recessed in an inside wall of the sheath opening 121, a truncated-cone-shaped socket 123 tapered forwardly from a cylindrical socket 124 recessed forwardly from the shoulder portion 13a of the syringe means 1 and communicating with the sheath opening 121, with the cylindrical socket 124 having an inside diameter larger than an inside diameter of a rear end portion of the truncated-cone-shaped socket 123, and the sheath opening 121 having an inside diameter equal to an inside diameter of a front end portion of the truncated-cone-shaped socket 123, thereby forming a tapered through hole 12a in the sleeve portion 12 as gradationally tapered forwardly from the shoulder portion 13a in the syringe means 1, the cylindrical socket 124, the truncated-cone-shaped socket 123, the ring groove 122 and the sheath opening 121.

The hollow needle assembly 2 includes: a hollow needle portion 21 having a tip end 211 formed on a front end of the hollow needle portion 21, a coupling sheath 212 formed on a rear portion of the hollow needle portion 21 having a stem socket 213 recessed inwardly forwardly to communicate with a needle hole 210 longitudinally formed through the hollow needle portion 21 and a female groove 214 spirally recessed in the stem socket 213: a shank portion 22 having a hollow truncated-cone-portion 22a engageable with the truncated-cone-shaped socket 123 in the sleeve portion 12, a packing ring 221 embedded in an inner ring groove 221a annularly recessed in a front portion of the truncated cone portion 22a and engageable with the ring groove 122 in the sleeve portion 12, a hollow stem portion 222 protruding forwardly from the truncated cone portion 22a having at least a male projection 223 circumferentially formed on the stem portion 222 to be engageable with the female groove 214 recessed in the coupling sheath 212 of the hollow needle portion 21 for detachably coupling the hollow needle portion 21 on the shank portion 22 secured on the syringe means 1 from outside the syringe cylinder 11 and an enlarged cylindrical portion 224 formed on a rear end portion of the shank portion 22 engageable with the cylindrical socket 124 in the sleeve portion 12; and a needle head portion 23 connected to the shank portion 22 by a hollow neck portion 24a and generally shaped as a circular disk having a rear arcuate surface of the needle head portion 23 and a central injection hole 231 formed therein to communicate with a venting slot 24 formed in the neck portion 24a and to communicate with a central through hole 220 longitudinally formed through the shank portion 22 and communicating with the needle hole 210 when coupling the hollow needle portion 21 on the shank portion 22, and a needle axis 200 defined in a central portion of the hollow needle assembly 2 and normally parallel with the syringe axis 100 when mounting the needle assembly 2 on the syringe means 1 for normal injection use. The liquid medicine 4 flows through the central injection hole 231, the venting slot 24, the central through hole 220 and the needle hole 210 to be injected into a patient's vein or blood vessel.

The plunger means 3 includes: a plunger 31 reciprocatively and straightly held in the syringe cylinder 11 with a flat portion 31a secantly formed on a periphery of the plunger 31 slidably engageable with the flat bore portion 10a for preventing a rotaton or twisting of the plunger 31 in the cylinder 11 about the syringe axis 100, a biasing socket 32 generally arcuate shaped and eccentrically recessed rearwardly from a plunger front surface 310 of the plunger 31 having a longitudinal axis 321 defined at a center of the socket 32 to be deviated from the syringe axis 100 with an acute angle A, a guiding port 33 eccentrically converging rearwardly from the plunger front surface 310 for communicating with the biasing socket 32 and having a port center 331 normally aligned with the needle axis 200 of the needle assembly 2 when mounted on the syringe means for slidably guiding the needle head portion 23 rearwardly through the guiding port 33 to be engaged into the biasing socket 32 for biasing the hollow needle portion 21 obliquely to orient the tip end 211 towards an angled wall portion 13b between the shoulder portion 13a and the cylinder 11 opposite to the sleeve portion 12 when retracting the needle assembly 2 within the hollow bore portion 10, a plunger rod 35 connected with the plunger 31 by coupling a coupling member 36 formed on a front end of the rod 35 with a recess 34 recessed in a rear portion of the plunger 31 and a rod handle 37 formed on a rear end of the rod 35 for grasping use, and a plunger axis 300 longitudinally defined in a central portion of the plunger 31 and the rod 35 to be aligned with the syringe axis 100 and to be parallel to the needle axis 200 when normally mounting the needle assembly 2 on the syringe means 1.

The shapes of the needle head portion 23 and the biasing socket 32 are not limited in this invention.

When using the present invention for injection use, the plunger 31 is pushed forwardly to drive the liquid medicine 4 into a patient's vein through the hollow needle portion 21 as shown in FIG. 6. After the medicine 4 is exhausted, the needle head portion 23 will be engaged with the biasing socket 32 in the plunger 31 as shown in FIG. 7 as urged by the rod 35.

Figure 9:
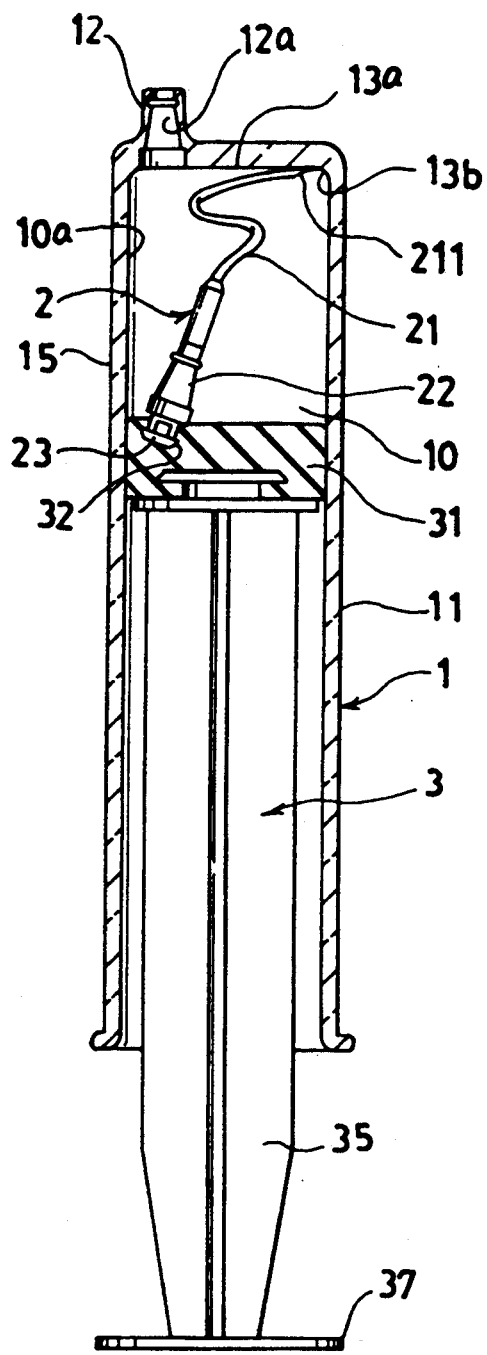
FIG. 9 is an illustration showing a bent needle in a syringe for preventing its outward re-protrusion in accordance with the present invention.
Figure 4:
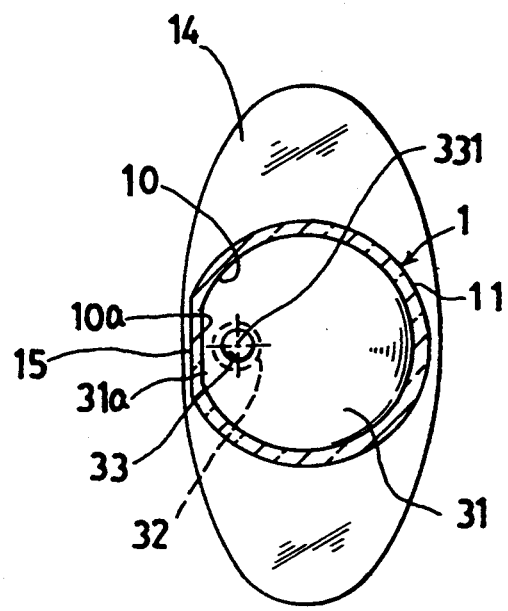
FIG. 4 is a cross sectional view of the present invention when viewed from 4—4 direction of FIG. 3.

When retracting the plunger 31 and the coupled needle assembly 2, the needle assembly 2 will be automatically biased as shown in FIG. 8, and while re-protruding of the needle portion 21 forwardly as shown in FIG. 9, the tip end 211 will be bent, without being protruded outwardly for preventing pricking on the user, the cleaners, or medical personnels.

The present invention is superior to the conventional safety syringe of U.S. Pat. No. 5,242,402 with the following advantages:

1. The hollow needle portion 21 may be detachably coupled to the shank portion 22 by rotating (T) the coupling sheath 212 to engage the female groove 214 in the sheath 212 with the projection 223 on the stem portion 222 of the shank portion 22 to conveniently install the needle portion 21 on the syringe means 1 outside the syringe means.

2. A variety of needles of different sizes may be replaceably mounted on the syringe means 1 for optional choices.

3. The structure is simplified to thereby reduce the production cost such as by eliminating the plug 13.

4. The tip end 211 is always biased towards the angled wall portion 13b opposite to the sleeve portion 12 to be far away from the through hole 12a so that the retracted needle assembly 2 will not be re-protruded outwardly, thereby absolutely ensuring a safety treatment of the retracted needle.

5. The truncated-cone shaped shank portion 22 of the needle assembly 2 will enforce a stable engagement with the through hole 12a in the sleeve portion 12, helpful for a smooth injection when urged by the plunger 31 for boosting liquid medicine into a patient during the injection.

6. The flat portion 15 of the syringe cylinder 11 will help a smooth intravenous injection on an ergonomic point of view.

7. The socket 32 is a "single hole", rather than an annular groove, thereby being stably engageable with the needle head portion 23 for a reliable coupling and retraction of the plunger 31 with the needle assembly 2 into the cylinder 11.

The present invention may be modified without departing from the spirit and scope of this invention.

I claim:

1. A safety syringe for intravenous injection comprising: a syringe means including: a syringe cylinder for filling liquid medicine therein, a syringe axis longitudinally defined in a central portion of the syringe cylinder, a sleeve portion eccentrically formed in a front portion of the cylinder contracted and tapered forwardly from a shoulder portion formed in a front portion of the cylinder between the syringe cylinder and the sleeve portion, and a flat bore portion longitudinally formed in said cylinder to have a cross section of secant circular shape of said bore portion;

a hollow needle assembly including a hollow needle portion detachably connected with a shank portion secured in the sleeve portion of said syringe means, and a needle head portion connected to the shank portion by a hollow neck portion, a central injection hole formed in said needle head portion, and a venting slot formed in the neck portion, said central injection hole and said venting slot communicating with a central through hole longitudinally formed through the shank portion and communicating with the needle hole formed in said hollow needle portion when coupling the hollow needle portion on said shank portion, and a needle axis defined in a central portion of the hollow needle assembly and normally parallel with the syringe axis when mounting the needle assembly on the syringe means for normal injection use; and a plunger means including: a plunger reciprocatively and straightly held in the syringe cylinder, a biasing socket eccentrically recessed rearwardly from a plunger front surface of the plunger having a longitudinal axis defined at a center of the biasing socket to be deviated from the syringe axis with an acute angle, a guiding port eccentrically converging rearwardly from the plunger front surface for communicating with the biasing socket and having a guiding port center aligned with the needle axis of said needle assembly when normally mounted on said syringe means for slidably guiding the needle head portion rearwardly through the guiding port to be engaged into the biasing socket for biasing the hollow needle portion obliquely towards a side portion of the shoulder portion opposite to the sleeve portion of the syringe means when retracting the needle assembly within the syringe cylinder, and a plunger rod connected with the plunger;

said plunger having a flat portion slidably straightly engageable with said flat bore portion secantly formed in said cylinder for preventing a free rotation of said plunger in said cylinder;

said sleeve portion including: a sheath opening formed in a front end portion of the sleeve portion, a ring groove annularly recessed in an inside wall of the sheath opening, a truncated-cone-shaped socket tapered forwardly from a cylindrical socket recessed forwardly from the shoulder portion of the syringe means and communicating with the sheath opening, with the cylindrical socket having an inside diameter larger than an inside diameter of a rear end portion of the truncated-cone-shaped socket, and the sheath opening having an inside diameter equal to an inside diameter of a front end portion of the truncated-cone-shaped socket for forming a tapered through hole in the sleeve portion as gradationally tapered forwardly from the shoulder portion in the syringe means, the cylindrical socket, the truncated-cone-shaped socket, the ringe groove and the sheath opening; and said hollow needle portion having a coupling sheath formed on a rear portion of the hollow needle portion having a stem socket recessed inwardly forwardly to communicate with the needle hole longitudinally formed through the hollow needle portion and a female groove spirally recessed in the stem socket; said shank portion having a hollow truncated-cone-portion engageable with the truncated-cone-shaped socket in the sleeve portion, a packing ring secured to a front portion of the truncated cone portion and engageable with the ring groove in the sleeve portion for retaining a front portion of the shank portion in said sleeve portion, a hollow stem portion protruding forwardly from the truncated cone portion having at least a male projection circumferentially formed on the stem portion to be engageable with the female groove recessed in the coupling sheath of the hollow needle portion for detachably coupling the hollow needle portion on the shank portion secured on the syringe means from outside the syringe cylinder and an enlarged cylindrical portion formed on a rear end portion of the shank portion engageable with the cylindrical socket in the sleeve portion.

2. A safety syringe according to claim 1, wherein said syringe means has a flat portion longitudinally formed on a bottom portion of said syringe cylinder having a cross section of a secant circular shape.

* * * * *